US007683095B2

(12) United States Patent
Guthrie et al.

(10) Patent No.: US 7,683,095 B2
(45) Date of Patent: *Mar. 23, 2010

(54) COMPOSITIONS AND METHODS OF TREATING, REDUCING AND PREVENTING CARDIOVASCULAR DISEASES AND DISORDERS WITH POLYMETHOXYFLAVONES

(75) Inventors: Najla Guthrie, London (CA); Elzbieta Maria Kurowska, Ontario (CA); John A. Manthey, Auburndale, FL (US)

(73) Assignees: The United States of America as represented by the Secretary of Agriculture, Washington, DC (US); KGK Synergize, Inc., London, ON (CA)

(*) Notice: Subject to any disclaimer, the term of this patent is extended or adjusted under 35 U.S.C. 154(b) by 0 days.

This patent is subject to a terminal disclaimer.

(21) Appl. No.: 10/854,063

(22) Filed: May 26, 2004

(65) Prior Publication Data
US 2004/0214882 A1 Oct. 28, 2004

Related U.S. Application Data

(63) Continuation of application No. 09/528,488, filed on Mar. 17, 2000, now Pat. No. 6,987,125, which is a continuation-in-part of application No. 09/167,634, filed on Oct. 6, 1998, now abandoned.

(51) Int. Cl.
*A61K 31/352* (2006.01)
*C07D 311/30* (2006.01)
(52) U.S. Cl. ............... 514/456; 514/457; 549/403
(58) Field of Classification Search .......... 514/456, 514/458, 457; 549/399, 403; 424/736
See application file for complete search history.

(56) References Cited

U.S. PATENT DOCUMENTS

| | | | | |
|---|---|---|---|---|
| 3,903,266 | A | * | 9/1975 | Robbins .................. 514/56 |
| 5,580,545 | A | * | 12/1996 | Washino et al. ............ 424/49 |
| 5,591,772 | A | * | 1/1997 | Lane et al. ............... 514/458 |
| 6,096,364 | A | | 8/2000 | Bok et al. ................ 426/590 |
| 6,239,114 | B1 | * | 5/2001 | Guthrie et al. ............. 514/32 |
| 6,251,400 | B1 | | 6/2001 | Guthrie et al. ............ 424/736 |
| 6,987,125 | B1 | | 1/2006 | Guthrie et al. ............ 514/456 |
| 2001/0055627 | A1 | * | 12/2001 | Guthrie et al. ............ 424/736 |
| 2002/0054924 | A1 | | 5/2002 | Leahy et al. ............. 424/732 |
| 2002/0090404 | A1 | | 7/2002 | Guthrie et al. ............ 424/755 |
| 2002/0090405 | A1 | | 7/2002 | Guthrie et al. ............ 424/755 |
| 2004/0152641 | A1 | | 8/2004 | Guthrie et al. ............. 514/27 |
| 2004/0176311 | A1 | | 9/2004 | Mo et al. ................. 514/27 |
| 2004/0241882 | A1 | | 10/2004 | Guthrie et al. ............ 514/456 |
| 2005/0227930 | A1 | | 10/2005 | Guthrie ................... 514/27 |

FOREIGN PATENT DOCUMENTS

| | | |
|---|---|---|
| CA | 2403548 | 9/2001 |
| WO | WO87/06833 | * 11/1987 |
| WO | WO99/52380 | * 4/1999 |
| WO | WO 0019998 | 4/2000 |
| WO | WO 0072862 | 12/2000 |
| WO | WO 0170029 | 9/2001 |
| WO | WO 0222145 | 3/2002 |
| WO | WO 0234072 | 5/2002 |
| WO | WO 02055071 | 7/2002 |
| WO | WO 2005096704 | 10/2005 |

OTHER PUBLICATIONS

Tatum, J. et al. "Six New Flavonoids from Citrus" Phytochemistry (1972) vol. 11, pp. 2283-2288.*
Carroll et al. "Dietary Fatty Acids, Tocotrienols, and Cancer" Journal of Food Lipids (1998) vol. 5, pp. 141-147.*
Wang et al. "Antimicrobial Flavonoids from *Psiadia trinervia* and their Methylated and Acetylated Derivatives" Phytochemistry (1989) vol. 23, No. 9, pp. 2323-2327.*
Sugiyama et al., "Studies on the Differentiation Inducers of Myeloid Leukemic Cells from Citrus species," Chemical and Pharmaceutical Bulletin (1993) vol. 41, No. 4, pp. 714-719.*
Remington: The Science and Practice of Pharmacy, twentieth edition, published 2000 by Lippincott Williams and Wilkins, Edited by Alfonso R. Gennaro. pp. 743-747 and 858-863.*
Iwase et al., "Inhibitory effect of Flavonoids from Citrus plants on Epstein-Barr virus activation and two-stage carcinogenesis of skin tumors" Cancer Letters (2000) vol. 154 pp. 101-105.*
Kurowska et al., "Hypolipidemic activities of tangeretin, a flavonoid from tangerine in vitro and in vivo", Annual Meeting of American Societies for Experimental Biology on Experimental Biology 2001, Mar. 7.
Kurowska et al., Hypolipidemic Effects and Absorption of Citrus Polymethoxylated Flavones in Hamsters with Diet-Induced Hypercholestrolemia: J Agr Food Chem 2004 vol. 52 p. 2879-2886.
Kerckhoffs D. Et al. "Effects on the Human Serum Lipoprotein Profile of beta-Glucan, Soy protein and Isoflavones, Plant Sterols and Stanols, Garlic and Tocotrienols" J Nutr Sep. 2002 vol. 132(9) p. 2494-2505.
Manthey, John et al., "Biological Properties of Citrus Flavonoids Pertaining to Cancer and Inflammation", Current Med Chem 2001 (8) (135-153).

* cited by examiner

*Primary Examiner*—Shaojia Anna Jiang
*Assistant Examiner*—Eric S Olson
(74) *Attorney, Agent, or Firm*—Lowenstein Sandler PC

(57) ABSTRACT

Compositions and methods for the treatment, reduction and/or prevention of cardiovascular diseases and disorders are described. Individuals at high risk for developing or having cardiovascular disease or disorder may be treated with an effective dose of a polymethoxyflavone including limocitrin derivatives, quercetin derivatives, naturally occurring polymethoxyflavones, tocotrienols, and mixtures of these compounds.

7 Claims, No Drawings

COMPOSITIONS AND METHODS OF TREATING, REDUCING AND PREVENTING CARDIOVASCULAR DISEASES AND DISORDERS WITH POLYMETHOXYFLAVONES

1. CROSS REFERENCE TO RELATED APPLICATIONS

This application is a continuation of U.S. application Ser. No. 09/528,488 filed Mar. 17, 2000 now U.S. Pat. No. 6,987, 125, which is a continuation-in-part of U.S. patent application Ser. No. 09/167,634, filed on Oct. 6, 1998 now abandoned entitled "Compositions and Methods of Inhibiting Neoplastic Diseases with Compounds Related to Limocitein and 5-Desmethyl Sinensetin", wherein the entire disclosure is herein incorporated by reference.

2. BACKGROUND OF THE INVENTION

A. Field of the Invention Reference

The present invention relates to compositions and methods for the prevention, reduction, and/or treatment of cardiovascular diseases with synthetic and naturally occurring polymethoxyflavone compounds derived, some of which are derived from limocitrin and quercetin.

These compounds include, but are not limited to, the following examples of limocitrin and quercetin derivatives:
limocitrin-3,7,4'-trimethylether (5-hydroxy-3,7,8,3',4'-pentamethoxyflavone)
limocitrin-3,5,7,4'-tetramethylether (3,5,7,8,3'4'-hexamethoxyflavone)
limocitrin-3,5,7,4'-tetraethylether (8,3'-dimethoxy-3,5,7,4'-tetraethoxylfavone)
limocitrin 3,7,4'-trimethylether-5-acetate
quercetin tetramethylether (5-hydroxy-3,7,3',4'-tetramethoxyflavone)
quercetin 3,5-dimethylether-7,3'4'-tribenzyl ether
quercetin pentamethylether (3,5,7,3',4'-pentamethoxyflavone)
quercetin-5,7,3',4'-tetramethylether-3-acetate
quercetin-5,7,3',4'-tetramethylether (3-hydroxy-5,7,3',4'-tetramethoxyflavone)

Examples, but not limited to, of naturally occurring polymethoxyflavones for the purposes of the present invention include:
3,5,6,7,8,3',4'-heptamethoxflavone
nobiletin (5,6,7,8,3',4'-hexamethoxyflavone)
tangeretin (5,6,7,8,4'-pentametlioxyflavone)
5-desmethylnobiletin (5-hydroxy-6,7,8,3'4'-pentamethoxyflavone)
tetra-O-methylisoscutellarein (5,7,8,4'-tetramethoxyflavone)
5-desmethylsinensetin (5-hydroxy-6,7,3',4'-tetramethoxyflavone)
sinensetin (5,6,7,3',4'-pentamethoxyflavone).

B. Description of the Related Art

Limocitrin derivatives are a group of citrus-derived flavonoids that are naturally occurring in the plant or are chemically synthesized. 5-desmethylsinesetin is chemically synthesized form of sinensetin (Tatum, J. H. et al., Phytochemistry II, 2283-2288, 1972). Sinensetin occurs in trace levels in mandarin orange leaves (Sugiyama, S. et al., Chem. Pharm. Bull., Volume 41, 714-719, 1993), and in orange and mandarin peel. Flavonoids are polyphenolic compounds that occur ubiquitously in foods of plant origin. The major dietary sources of flavonoids are vegetables, fruits, and beverages such as tea and red wine (Hertog, M. G. L. et al., J. Agric. Food Chem. Volume 41, 1242-1246, 1993). Flavonoids have been demonstrated to be the most potent dietary antioxidants and in light of the large dietary consumption, flavonoids make a major contribution to the antioxidant potential of the human diet. The main food sources of flavonols and flavones are black tea, onions, apples, herbs, and spices such as cloves and black pepper (Hertog. M. G. L., et al, J. Agric. Food Chem., Volume 40, 2379-2383, 1992).

The association between quercetin and cardiovascular disease has been studied in prospective cohort studies and cross-cultural epidemiological studies. Flavonol and flavone intake was inversely associated with mortality from coronary heart disease and to a lesser extent with incidence of first myocardial infarction. These effects were independent of known risk factors for coronary heart disease such as serum cholesterol, body mass index, blood pressure, smoking and intake of antioxidant vitamins, alcoiol, and fat. Flavonol and flavone intake (mainly quercetin) was also inversely associated with stroke risk (Hertog et al., Lancet, Volume 324, 1007-1011, 1993; Keli et al., Arch. Inter. Med., Volume 154, 637-642, 1996). However, four thousand different types of flavonoids have been described and it is crucial that the active components be identified not only to make a positive impact on agriculture but also to more specifically use these nutraceuticals as anticholesterol agents and/or antithrombotic, anti-coronary heart disease, antimyocardial infarction and/or anti-stroke agents.

In the United States, the complications of atherosclerosis account for about one half of all deaths and for about one third of deaths in persons between 35 and 65 years of age. Atherosclerosis, or the developments of atheromatous plaques in large and medium-sized arteries, is the most common form of arteriosclerosis. Many factors a re associated with the acceleration of atherosclerosis, regardless of the underlying primary pathogenic change, for example, age, elevated plasma cholesterol level, high arterial blood pressure, cigarette smoking, reduced high-density lipoprotein (HDL) cholesterol level, or family history of premature coronary artery disease.

The risk of death from coronary artery disease has a continuous and graded relation to total serum cholesterol levels greater than 180 mg/dl (Stamler et al., JAMA, Volume 256, 2823, 1986). Approximately one third of adults in the United States have levels that exceed 240 mg/dl and, therefore, have a risk of coronary artery disease that is twice that of people with cholesterol levels lower than 180 mg/dl. Acceleration of atherosclerosis is principally correlated with elevation of LDL, or beta fraction, which is rich in cholesterol but poor in triglycerides, Elevation of HDL or alpha fraction, has a negative correlation with atherosclerosis (Castelli et al., JAMA, Volume 256, 2835, 1986). HDL exerts a protective effect and the ratio of total cholesterol to HDL cholesterol is a better predictor of coronary artery disease than the level of either alone. Total cholesterol levels are classified as being desirable (<200 mg/dl), borderline (200-239 mg/dl), or high (>240 mg/dl) (Report of the National Education Expert Panel on Detection, Evaluation, and Treatment of High Blood Cholesterol in Adults, Arch. Intern. Med., Volume 148, 36, 1988).

Advances in the study of cholesterol metabolism and coronary disease have initiated an era of increased emphasis on preventive therapy. New guidelines for the detection and treatment of high blood cholesterol in adults recommend that patients with high cholesterol levels or with borderline-high levels and two or more additional risk factors should have a measurement of LDL. LDL cholesterol levels are then classified as borderline-high risk (130-159 mg/dl) or high risk (>160 mg/dl). Dietary treatment is recommended for those patients with high-risk levels who have two or more additional risk factors. Drug treatment is recommended for all patients with LDL levels greater than 189 mg/dl and for those patients with LDL cholesterol levels between 159 and 189 mg/dl who have two or more additional risk factors. Among the many drugs that have been used to reduce serum cholesterol levels are cholestyramine, colestipol, clofibrate, gemfibrozil, and lovastatin.

Platelet-blood vessel interactions are implicated in the development of thrombosis. Flavonoids inhibit platelet aggregation and adhesion (Frankel et al., Lancet, Volume 341, 1103-1104, 1993). Flavonoids antagonize thromboxane formation and increase platelet cyclic AMP levels. This is important because flavonoids additionally scavenge free radicals and their antioxidant actions participate in their antithrombotic action (Gryglewski et al., Biochem. Pharmacol., Volume 36, 317-322, 1987). Drug treatment is recommended for patients with thrombosis and ischemic heart disease. The medical therapy comprises pharmaceutical drugs including, but is not limited to, aspirin (anti-platelet aggregating agents) and the combined use of beta-adrenergic blocking agents (e.g. propranonol, nadolol, timolol, etc.), nitrates (e.g., nitroglycerin) and calcium channel blockers (e.g., verapamil, nifedipine, diltiazem, etc.).

There remains a need in the art for methods and compositions for at least reducing the development of and/or treating vascular diseases. The present invention provides new compositions and methods directed to this need. The use of limocitrin derivatives, quercetin derivatives and/or, naturally-occurring polymethoxyflavones and mixtures thereof alone or in combination with a cholesterol-lowering drug has not been reported for at least reducing the development of and/or treating vascular diseases and disorders.

3. SUMMARY OF THE INVENTION

It is therefore an object of the present invention to provide compositions and methods for the reduction, prevention, and/or treatment of cardiovascular diseases and disorders wherein an effective amount of a composition having at least one limocitrin and/or quercetin derivative is administered to reduce, prevent or treat a mammal at high risk for or suffering from a cardiovascular disease.

Another object of the present invention is to provide compositions and methods for the reduction, prevention, and/or treatment of cardiovascular diseases or disorders wherein an effective amount of a composition having at least one flavonoid is administered to reduce, prevent or treat a mammal at high risk for or suffering from a cardiovascular disease.

A further object of the present invention is to provide compositions and methods for the reduction, prevention, and/or treatment of cardiovascular diseases or disorders wherein an effective amount of a composition having at least one limocitrin, quercetin derivative, tocotrienol, and mixtures thereof is administered to reduce, prevent or treat a mammal at high risk for or suffering from a cardiovascular disease.

A still further object of the present invention is to provide compositions and methods for the reduction, prevention, and/or treatment of cardiovascular diseases or disorders wherein an effective amount of a composition having at least one naturally occurring polymethoxyaflavone is administered to reduce, prevent, or treat a mammal at high risk for or suffering from a cardiovascular disease.

Another object of the present invention is to provide compositions and methods for the reduction, prevention, and/or treatment of cardiovascular diseases or disorders wherein an effective amount of a composition having at least one naturally occurring polymethoxyflavone, tocotrienols, and mixtures thereof, is administered to reduce, prevent or treat a mammal at high risk for or suffering from a cardiovascular disease.

A further object of the present invention is to provide compositions and methods for the reduction, prevention, and/or treatment of cardiovascular diseases or disorders wherein an effective amount of a composition having at least one a tocotrienol, flavonoid, and mixtures thereof, is administered to reduce, prevent, or treat a mammal at high risk for or suffering from a cardiovascular disease.

A still further object of the present invention is to provide compositions and methods for the reduction, prevention, and/or treatment of cardiovascular diseases or disorders wherein an effective amount of a composition having at least one limocitrin derivative, quercetin derivative, naturally occurring polymethoxyaflavone, tocotrienol, and mixtures thereof, is administered to a mammal to lower serum cholesterol, apo-B, and/or LDL cholesterol.

Another object of the present invention is to provide compositions and methods for the reduction, prevention, and/or treatment of cardiovascular diseases or disorders wherein an effective amount of a composition having at least one limocitrin derivative, quercetin derivative, naturally occurring polymethoxyaflavone, tocotrienol, and mixtures thereof, in combination with a cholesterol-lowering drug, is administered to a mammal to lower serum cholesterol, apo-B, and/or LDL cholesterol Another object of the present invention is to provide compositions and methods for the reduction, prevention, and/or treatment of cardiovascular diseases or disorders wherein an effective amount of a composition having at least one limocitrin derivative, quercetin derivative, naturally occurring polymethoxyaflavone, tocotrienol, and mixtures thereof, in combination with a pharmaceutical drug including anti-platelets agents, beta-adrenergic blocking agents, nitrates or calcium channel blockers.

Further objects and advantages of the present invention will become apparent from the following description.

4. DETAILED DESCRIPTION OF THE INVENTION

The present invention relates to the use of at least one of limocitrin derivative, quercetin derivative, polymethoxyflavone, tocotrienol and mixtures thereof alone or in combination with at least one cholesterol-lowering drug for the treatment of cardiovascular diseases or disorders. Limocitrin occurs in the peel of lemon as limocitrin-3-O-glucoside, and can be produced from the 3-glycoside by enzymatic and acid hydrolysis (Horowitz et al., J. Org. Chem., Volume 25, 21885-21887, 1960) or by a chemical synthesis procedure such as reported by Dryer et al., Tetrahedron, Volume 20, 2977-2983, 1964. Two limocitrin analogues, limocitrin 3,7,4'-trimethylether and limocitrin-3,5,6-4'-tetramethylether, also occur in orange peel (Tatum et al., Phytochemistry, volume II, 2283-2288, 1972). Several polymethoxyflavones were tested and found to be active as inhibitors of apolipoprotein B (apoB) production and had negligible cytotoxicity in the human liver carcinoma cell line HepG2. It has been shown that humans with coronary heart disease (CAD) have higher levels of apoB in their blood. ApoB concentrations also reflect the number of LDL, and VLDL (very low density lipoprotein) particles in arteries. Administering polymethoxylatedflavone of the invention to a mammal results in a reduction in the amount of substances in the blood which contribute to CAD, such as for example apoB, LDL, cholesterol, etc; preferably reduction of the serum, plasma, or whole blood concentration or in vivo amounts of these substances. Preferably the concentration or in vivo amount of these substances is reduced to normal levels typically found in such a mammal. Also, preferably, the polymethoxylatedflavone of the present invention are administered in amounts which produce little or no cytotoxicity, more preferably where no cytotoxicity is produced.

The present invention is also directed to compositions and methods for the prevention and treatment of neoplastic cells and diseases with flavonoid and limocitrin compounds.

By way of definition, a polymethoxylatedflavone is a flavone substituted with methoxy groups, preferably at least 2, more preferably at least 3, more preferably at least 4, more preferably 4-8, and most preferably 4-7 methoxy groups and optionally substituted by one or more hydroxy groups, preferably 1-3, and more preferably 1-2 hydroxy groups.

Four compounds of the present invention were synthesized from the lemon flavonoid limocitrin (3',8-dimethox-3,5,7,4'-tetrahydroxyflavone) for use in the present invention: limocitrin-3,7,4'-trimethylether (5-hydroxy-3,7,8,3',4'-pentamethoxyflavone); limocitrin-3,5,7,4'-tetramethylether (3,5,7,8,3'4'-hexamethoxyflavone); and limocitrin-3,7,4'-trimethylether-5-acetate.

A number of methoxylated flavones, most of which occur naturally in citrus, have been found to be useful in the present invention. Also included are substituted derivatives of quercetin. The compounds in these groups include 5-desmetlhymobiletin (5-hydroxy-6,7,8,3',4'-pentamethoxyflavone); tetra-O-methylisoscutellarein (5,7,8,4'-tetramethoxyflavone); 3,5,6,7,8,3',4'-heptamethoxyflavone; nobiletin (5,6,7,8,3',4'-hexamethoxyflavone); tangeretin (5,6,7,8,4'-pentamethoxyflavone); sinensetin (5,6,7,3',4'-pentamethoxyflavone); 5-desmethylsinensetin (5-hydroxy-6,7,3',4'-tetramethoxyflavone); quercetin tetramethylether (5-hydroxy-3,7,3',4'-tetramethoxyflavone); quercetin 3,5-dimethylether-7,3',4'-tribenzylether; quercetin pentamethyl ether (3,5,7,3',4'-pentamethoxyflavone); quercetin-5,7,3',4'-tetramethylether-3-acetate; quercetin-5,7,3',4'-tetramethylether (3-hydroxy-5,7,3',4'-tetramethoxyflavone).

The basic structures for limicitrin derivatives and 5-desmethylsinensetin are represented below:

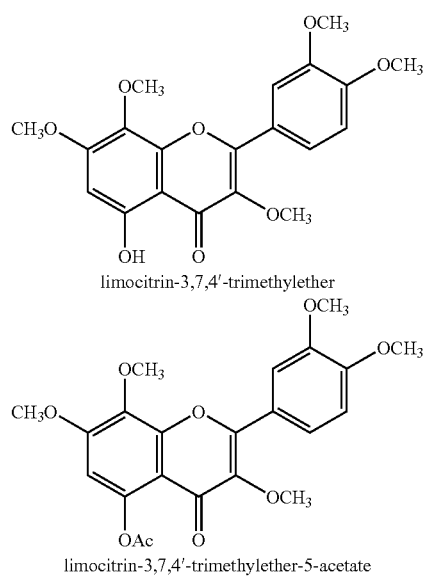

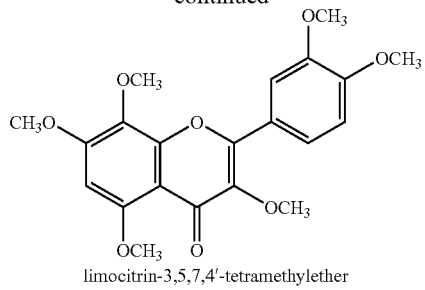
limocitrin-3,5,7,4'-tetramethylether

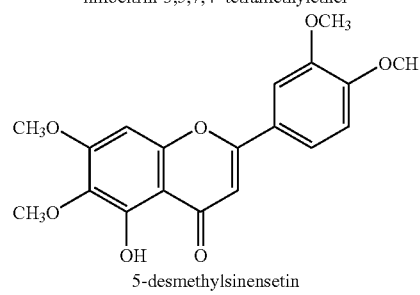
5-desmethylsinensetin

Examples of tocotrienol compounds useful in the present invention include, but are not limited to, are alpha-tocotrienol, gamma-tocotrienol, delta-tocotrienol, and mixtures thereof.

Examples of cholesterol-lowering drugs for the treatment of cardiovascular diseases or disorders useful in the present invention include, but are not limited to, are cholestyramine, colestipol, clofibrate, gemfibrozil or lovastatin.

The methods of the present invention may be administered to any mammal. Most preferably, the polymethoxylatedflavone useful in the methods of the present invention are administered to humans.

In another aspect of the present invention, the polymethoxylatedflavone may be formulated into a pharmaceutical preparation by a conventional method usually employed in the art.

Dosages for the compositions of the present invention may be formulated into pharmaceutical preparations for administration to mammals for reduction, prevention, and treatment of cardiovascular diseases. Examples, not limited thereto, of cardiovascular disease treatable by the compositions of the present invention include hypercholesterolemia, hyperlipidemia, atherosclerosis, thrombosis, myocardial infarction, etc Many of the limocitrin derivatives, quercetin derivatives, naturally-occurring polymethoxyflavones, tocotrienol compounds and mixtures thereof may be provided as compounds with pharmaceutically compatible counterions, a form in which they may be soluble. Counterions for the purposes of this invention include, for example, hydrophilic and hydrophobic agents.

The polymethoxylatedflavone can be administered by a variety of routes, including oral, transdermal, rectal, intrarticular, intravenous, and intramuscular introduction. However, it should be understood that the amount of the polymethoxylatedflavone actually administered ought to be determined in light of various relavent factors including the condition to be treated, the chosen route of administration, the age and weight of the individual patient, and the severity of the patient's condition, and therefore, the doses given herein should not be construed to limit the scope of the invention in any way. The polymethoxylatedflavone useful in the present invention may be administered in a pharmaceutically or physiologically acceptable carrier. The pharmaceutically or physiologically acceptable carrier is any solvent with which the polymethoxylatedflavone is compatible and which is non-toxic to individuals treated at the amounts administered. A variety of delivery systems for pharmacological compositions may be employed including, but not limited to, liposomes and emulsions. The pharmaceutical compositions also may comprise suitable solid or gel phase carriers or excipients. Examples of excipients include, but are not limited to, calcium carbonate, calcium phosphate, various sugars, starches, cellulose derivatives, gelatin, and polymers such as polyethylene glycols.

Formulations suitable for oral administration include liquid solutions of the active compound or compounds dissolved in a diluent such as, for example, saline, water, PEG 400; solid preparations such as capsules or tablets, each containing a predetermined amount of the active agent as solids, granules, gelatins, suspensions, and/or emulsions.

Formulations suitable for parenteral administration include aqueous and non-aqueous isotonic sterile solutions which contain buffers, antioxidants, and preservatives. The formulations may be in unit dose or multi-dose containers.

Dosages administered are any effective amount of a polymethoxylatedflavone which will, when given for the treatment, prophylactically or therapeutically, reduce or prevent cardiovascular diseases by reducing levels of substances which contribute to cardiovascular diseases to normal or near normal levels in the blood or in vivo. By way of definition substances which contribute to cardiovascular diseases, include but are not limited to apoprotein B, low density lipoproteins, very low density lipoproteins, cholesterol, etc.

Patient dosages for oral administration of flavonoids range from about 1-1000 mg/day, commonly 1-500 mg/day, and typically 1-100 mg/day. Stated in terms of patient with a 70 kg body weight, usual dosages range from about 0.01-15 mg/kg/day, commonly from about 0.01-7.0 mg/kg/day, and typically from about 0.01-2.0 mg/kg/day.

Patient dosages for oral administration of synthetic flavonoid analogues range from about 2000-5000 mg/day, commonly from about 1000-2000 mg/day, and typically from about 500-1500 mg/day.

Patient dosages for oral administration of limocitrin derivatives, quercetin derivatives, naturally-occurring polymethoxyflavones, and tocotrienols range from about 1-1000 mg/day, commonly about 1-500 mg/day, and typically from about 1-100 mg/day.

Patient dosages for oral administration of synthetic limocitrin derivatives range from about 200-500 mg/day, commonly about 1000-2000 mg/day, and typically from about 500-1500 mg/day.

Patient dosages for oral administration of naturally-occurring polymethoxyflavones range from about 1-1000 mg/day, commonly from about 1-500 mg/day, and typically from about 1-100 mg/day. Stated in terms of patient body weight, for about 70 kg body weight, usual dosages range from about 0.01-15 mg/kg/day, commonly from about 0.01-7.0 mg/kg/day, and typically from about 0.01-2.0 mg/kg/day.

Dosage amount and interval may be adjusted individually to provide plasma levels of the active moiety which are sufficient to maintain the anti-proliferative and antioxidative effects of the disease being treated.

For local administration, the composition can be administered by injection directly into a tissue, often in a depot or sustained release formulation.

The following examples illustrate the use of the invention for lowering substances which contribute to cardiovascular diseases and disorders. They are intended to further illustrate the invention and are not intended to limit the scope of the invention as defined by the claims.

EXAMPLE 1

Limocitrin derivatives, quercetin derivatives, naturally occurring polymethoxyflavones, and tocotrienols were tested for cholesterol lowering activity in HepG2 cells. Confluent HepG2 cells were preincubated for 24 hours in a lipoprotein-free medium (Minimum Essential Medium (MEM), Life Technologies, Burlington, Canada) in which the fetal bovine serum (Life Technologies, Burlington, Canada) was replaced by bovine serum albumin (BSA, Life Technologies, Burlington, Canada) to inhibit cell proliferation and to stimulate synthesis of cholesterol-containing lipoproteins. Cells were subsequently incubated for another 24 hours in the same medium in the presence or absence of limocitrin derivatives, quercetin derivatives, naturally occurring polymethoxyflavones, or tocotrienols (See Table 1) at the highest concentrations sustaining about 100%±10% cell viability, as determined by the 3-(4,5-dimethylthiazol-2-yl)-2,5-diphenyltetrazolium bromide (MTT) viability assay. The test compounds were added to the cell culture medium after solubilization in dimethyl sulfoxide (DMSO) and filter sterilized. The final concentration of DMSO in culture media did not exceed 0.3% by volume, to prevent any effects of DMSO on apo B metabolism. For each experiment, equal concentrations of solvent were added to all treatment media and to a control medium (without tested compounds). At the end of the incubation, culture media were collected and the concentration of the LDL structural protein, apo-B, was measured by ELISA. The competitive Elisa assay kit for determination of human apo B (Ortho Diagostics, LaJolla, Calif.) measures medium apo B concentrations within the range 0.4-0.031 µg/mL. In this assay, microtiter 96-well plates are coated with monoclonal antibody against human apo B, which binds apo B epitope from human LDL (standard curve, control sera with high and low content of human apo B) or from LDL-like lipoproteins secreted by HepG2 cells (tested media, usually 2× diluted with $Ca^{2+}$- and $Mg^{2-}$-free phosphate buffered saline (PBS)). After the exposure, a fraction of antibody is blocked and the remaining amount is captured by a subsequent incubation with conjugate containing a secondary antibody (against anti-human apo B) coupled with horseradish peroxidase. The following incubation with horseradish peroxidase substrate, o-phenylenediamine, produces a yellow color change proportional to the amount of apo B present, and the optical density of samples is measured at 490-492 nm against the blank PBS/conjugate wells. To determine whether evaluated compounds cross-react with Elisa assay, in separate study, various doses of compounds were tested in presence of cell-free culture media.

Amount of lipoprotein-associated apo-B in the media net apo-B secretion) was determined as described above, and calculated per mg cell protein. Net apo B3 secretion was also expressed as percent of control (amount of apo B in medium from cells incubated without tested compounds).

TABLE 1

IC$_{50}$ concentrations were 2.5 µg/mL for tangeretin, 4.9 µg/mL for nobiletin, 7.8 µg/mL for heptamethoxyflavone and 17.8 µg/mL for sinensetin.

| Compound | Concentration µg/mL medium | Apo B µg/mL medium | % apo B in medium | % apo B reduction |
|---|---|---|---|---|
| 5, 6, 7, 8, 4'-pentamethoxyflavone | 0 | 0.252 ± 0.20 | 100 ± 4 | — |
| | 3.12 | 0.080 ± 0.02 | 32 ± 8 | 68 |
| | 6.25 | 0.055 ± 0.01 | 22 ± 2 | 78 |
| | 12.5 | 0.048 ± 0.01 | 19 ± 2 | 81 |
| | 25.0 | 0.035 ± 0.01 | 14 ± 1 | 86 |
| 5, 6, 7, 8, 3', 4'-hexamethoxyflavone | 0 | 0.55 ± 0.21 | 100 ± 15 | — |
| | 6.25 | 0.37 ± 0.09 | 67 ± 16 | 33 |
| | 12.5 | 0.175 ± 0.03 | 32 ± 6 | 68 |
| | 25.0 | 0.10 ± 0.01 | 18 ± 1 | 82 |
| | 50.0 | 0.095 ± 0.01 | 17 ± 1 | 83 |
| Heptamethoxyflavone | 0 | 0.250 ± 0.02 | 100 ± 8 | — |
| | 6.25 | 0.138 ± 0.02 | 55 ± 5 | 45 |
| | 12.5 | 0.080 ± 0.02 | 32 ± 9 | 68 |
| | 25.0 | 0.048 ± 0.01 | 19 ± 3 | 81 |
| | 50.0 | 0.045 ± 0.01 | 18 ± 2 | 82 |
| Sinensetin | 0 | 0.93 ± 0.07 | 100 ± 7 | — |
| | 6.25 | 0.70 ± 0.13 | 75 ± 14 | 25 |
| | 12.5 | 0.54 ± 0.04 | 58 ± 4 | 42 |
| | 25.0 | 0.35 ± 0.04 | 38 ± 5 | 62 |
| | 50.0 | 0.26 ± 0.02 | 28 ± 5 | 72 |
| Tetra-O-methyl-Scutellarein | 0 | 0.430 ± 0.01 | 100 ± 10 | — |
| | 6.25 | 0.305 ± 0.03 | 71 ± 7 | 29 |
| | 12.5 | 0.255 ± 0.06 | 59 ± 13 | 41 |
| 5-desmethyl-sinensetin | 0 | 1.15 ± 0.29 | 100 ± 25 | — |
| | 25.0 | 0.84 ± 0.21 | 73 ± 18 | 27 |
| | 50.0 | 0.41 ± 0.20 | 36 ± 1 | 64 |

The three naturally occurring polymethoxyflavones tested have a dose-response inhibitory effect on apo-B production. These results along with other preliminary studies indicate that the following compounds when used either alone or in combination have inhibitory effects on apo-B production: the limocitrin and quercetin derivatives: limocitrin-3,7,4'-trimethylether (5-hydroxy-3,7,8,3',4'-pentamethoxyflavone); limocitrin-3,5,7,4'-tetramethylether (3,5,7,8,3',4'-hexamethoxyflavone); limocitrin-3,5,7,4'-tetraethylether (8,3'-dimethoxy-3,5,7,4'-hexamethoxyflavone); limocitrin-3,7,4'-trimethylether-5-acetate; quercetin tetramethylether (5-hydroxy-3,7,3',4'-tetramethoxyflavone); quercetin-3,5-dimethylether-7,3',4'-tribenzyl ether; quercetin pentamethyl ether (3,5,7,3',4'-pentamethoxyflavone); quercetin-5,7,3',4'-tetramethylether-3-acetate; and quercetin-5,7,3',4'-tetramethylether (3-hydroxy-5,7,3',4'-tetramethoxyflavone); and the naturally occurring polymethoxyflavones: 3,5,6,7,8,3',4'-heptan-ethoxyflavone; nobiletin (5,6,7,8,3',4'-hexamethoxyflavone); tangeretin (5,6,7,8,4'-pentamethoxyflavone); 5-desmethylnobiletin (5-hydroxy-6,7,8,3',4'-pentamethoxyflavone); tetra-O-methylisoscutellarein (5,7,8,4'-tetramethoxyflavone); 5-desmethylsinensetin (5-hydroxy-6,7,3',4'-tetramethoxyflavone); and sinensetin (5,6,7,3',4'-pentamethoxyflavone).

The present invention is not to be limited in scope by embodiments disclosed in the examples that are intended illustration purposed and any methods which are functionally equivalent are within the scope of the invention. Various modifications of the invention in addition to those shown and described herein will become apparent to one of ordinary skill in the from the foregoing description. Such modifications are intended to fall within the scope of the appended claims. The various publications cited herein are herein incorporated by reference in their entirety.

We claim:

1. A method of lowering serum cholesterol, Apo B or LDL cholesterol comprising orally administering to a mammal having elevated levels of serum cholesterol, Apo B or LDL cholesterol an oral pharmaceutical dosage form selected from the group consisting of a tablet or a capsule, said dosage form comprising at least one pharmaceutically acceptable excipient and a combination of
    (a) at least one limocitrin derivative selected from the group consisting of limocitrin-3,7,4'-trimethylether; limocitrin-3,5,7,4'-tetramethylether; and limocitrin-3,7,4'-trimethylether-5-acetate, and
    (b) at least one quercetin derivative selected from the group consisting of quercetin tetramethylether; quercetin 3,5-dimethylether-7,3',4'-tribenzylether; quercetin pentamethylether; quercetin-5,7,3',4'-tetramethylether-3-acetate; and quercetin-5,7,3',4'-tetramethylether;
    to provide about 1-1000 mg/day limocitrin derivative and about 1-1000 mg/day quercetin derivative.

2. The method of claim 1, wherein the dosage form further comprises at least one tocotrienol and wherein the administration provides an amount of said dosage form to provide about 1-1000 mg/day tocotrienol.

3. The method of claim 1, wherein the tablet or capsule contains a predetermined amount of the mixture as solids, gelatins, suspensions or emulsions.

4. The method of claim 1, wherein the pharmaceutical acceptable excipient is a gel phase carrier.

5. The method of claim 1, wherein the pharmaceutically acceptable excipient is selected from the group consisting of calcium carbonate, calcium phosphate, a sugar, a starch, a cellulose derivative, gelatin and a polymer.

6. The method of claim 1, wherein the dosage form further comprises at least one polymethoxyflavone and wherein the administration provides an amount of said dosage form to provide about 1-1000 mg/day polymethoxyflavone.

7. The method of claim 1, wherein said mammal is a human.

* * * * *